United States Patent [19]

Einig et al.

[11] Patent Number: 5,230,901

[45] Date of Patent: Jul. 27, 1993

[54] SUSTAINED RELEASE TABLET OF A MIXTURE OF ALGINATES AND POLYACRYLATES

[75] Inventors: Heinz Einig, Neustadt; Baerbel Stieren, Mannheim; Volker Buehler, Karlsruhe; Matthias Hollmann, Weisenheim am Sand, all of Fed. Rep. of Germany

[73] Assignee: Knoll AG, Ludwigshafen, Fed. Rep. of Germany

[21] Appl. No.: 966,576

[22] Filed: Oct. 26, 1992

Related U.S. Application Data

[63] Continuation of Ser. No. 655,200, Feb. 14, 1991, abandoned, which is a continuation of Ser. No. 321,276, Mar. 9, 1989, abandoned.

[30] Foreign Application Priority Data

Mar. 23, 1988 [DE] Fed. Rep. of Germany ....... 3809764

[51] Int. Cl.$^5$ .......................... A61K 9/22; A61K 9/26; A61K 9/32
[52] U.S. Cl. ................................... 424/468; 424/486; 424/487; 424/488
[58] Field of Search ................ 424/468, 487, 488, 486

[56] References Cited

U.S. PATENT DOCUMENTS 4,784,858  11/1988  Ventouras .......................... 424/468

FOREIGN PATENT DOCUMENTS

| | | |
|---|---|---|
| 1184497 | 3/1985 | Canada . |
| 0063266 | 10/1982 | European Pat. Off. . |
| 0159604 | 10/1982 | European Pat. Off. . |
| 0122815 | 4/1984 | European Pat. Off. ............ 424/487 |
| 0213083 | 3/1987 | European Pat. Off. . |
| 0290229 | 11/1988 | European Pat. Off. . |
| 2820851 | 12/1978 | Fed. Rep. of Germany . |

OTHER PUBLICATIONS

1184497, Mar. 26, 1985 Canada.
1566935, May 8, 1980, Great Britain.
Rohm Pharma GmbH, Darmstadt, Germany.
Eudragit ®, Eudragit NE 30D and Eudragit L30D, Wassrige Acrylharzdispersionen (2 pages).
Rohm Pharma GmbH, Darmstadt, Germany, Eudragis ® RL 30 D und RS 30 D Anwendung in der Arzneimittelherstellung (pg. 1).
Rohm Pharma GmbH, Darmstadt, Germany, Eudragit ® NE 30 D, Anwending in der Arzneimittelherstellung (pg. 1).
Rohm Pharma GmbH, Darmstadt, Germany, Eudragit ® E fur Schnellzerfallende Filmuberzuge (pg. 1).

*Primary Examiner*—Lester L. Lee
*Assistant Examiner*—Donna M. Fox
*Attorney, Agent, or Firm*—Oblon, Spivak, McClelland, Maier & Neustadt

[57] ABSTRACT

A mixture of an alginate and a polyacrylate in a ratio of from 15:1 to 1:2 is suitable for the preparation of depot drug forms.

1 Claim, No Drawings

SUSTAINED RELEASE TABLET OF A MIXTURE OF ALGINATES AND POLYACRYLATES

This application is a continuation of application Ser. No. 07/655,200, filed on Feb. 14, 1991, now abandoned, which is a continuation of application Ser. No. 07/321,276, filed on Mar. 9, 1989, now abandoned.

The present invention relates to a mixture of alginates and polyacrylates and its use in the preparation of depot drugs.

It is known that alginates can be used for the preparation of depot drugs (Pharm. Ind. 33 (1971), 296). However, the use of alginates for this purpose often presents difficulties. For example, the formulations frequently do not achieve sufficient hardness when tableted. Their abrasion is therefore very high, which presents problems during subsequent film coating. Insufficient hardness leads to breaking during filling on filling machines. Furthermore, alginates readily absorb water, which leads to swelling of the tablets or, in the case of film tablets, to cracking of the films, unless complete protection from moisture is ensured by complicated and expensive packaging.

Conventional alginate-based sustained-release tablets show no plasma level having a pronounced plateau character, despite zero order in vitro release, and still show a pronounced and not always desirable plasma peak despite a substantial delay in the time of maximum plasma concentration compared with drug forms which release the active compound rapidly.

We have found that these difficulties can be avoided if polyacrylates or polymethacrylates are mixed with the alginates.

The present invention relates to a mixture of an alginate and a polyacrylate, polymethacrylate or copolymer of acrylic and methacrylic acid in a ratio of from 15:1 to 1:2, preferably 9:1 to 2:1, and its use for the preparation of depot drugs.

Particularly suitable alginates are propylene glycol alginates and alkali and alkaline earth metal alginates, in particular the sodium, potassium, ammonium and calcium alginates. These alginates are described, for example, in the book by Roy L. Whistler, Industrial Gums, New York, 1973, in the subsection by McNeely and Pettitt on alginates. They are mainly used as gel formers or thickeners in food technology, in the printing, textile and paper industries and in welding electrodes.

Particularly suitable polyacrylates are those of the formula

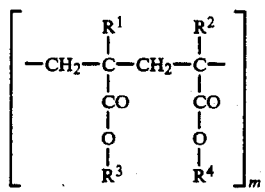

where $R^1$ and $R^2$ are each hydrogen or $C_1$-$C_4$-alkyl, $R^3$ is hydrogen, $C_1$-$C_4$-alkyl or a radical $-(CH_2)_n-NR^5R^6$ or $-(CH_2)_n-N^{\oplus}R^5R^6R^7\ Cl^{\ominus}$, where n is from 1 to 4 and $R^5$, $R^6$ and $R^7$ are each hydrogen or $C_1$-$C_4$-alkyl, $R^4$ is hydrogen or $C_1$-$C_4$-alkyl and m is from 500 to 1,500.

Such polyacrylates or methacrylates and copolymers are described in, for example, Houben-Weyl, Methoden der organischen Chemie, Thieme-Verlag, Stuttgart, 1961. Products which are commercially available under the name Eudragit ® are particularly suitable.

If the polyacrylate is used in the form of the ammonium salt ($R^3 = -(CH_2)_n-N^{\oplus}R^5R^6R^7\ Cl^{\ominus}$), m is preferably from 7,000 to 11,000, in particular from 8,000 to 10,000. In the other cases, m is preferably from 700 to 1,000.

The novel mixture is particularly suitable for the preparation of oral depot forms of propafenone, barucainide, nesapidil, gallopamil and biperiden.

The use of the novel mixture has the following advantages:

1. The release of the active compound from the drug forms is substantially linear.
2. The tablet cores are very hard and abrasion-resistant, so that they can be further processed without difficulties.
3. The hygroscopicity of the alginates is no longer disadvantageous during tablet preparation. The tableting mixtures can be pressed directly without granulation, and the expensive and complicated wet granulation can be avoided. Film tablets no longer require any special protection from moisture and no longer crack during open storage for a short time.
4. After administration of the novel drug forms, the plasma level of active compound has a pronounced plateau character and a substantially flatter curve than after administration of drug forms which are only based on alginates.

The Examples which follow illustrate the invention.

The ®Eudragit products used therein are described in the brochures Eudragit, E, L/S, RS, RL/RS, NED, LD from Röhm Pharma GmbH, Darmstadt.

EXAMPLE 1

Tablets having the following composition (in mg) were prepared in a conventional manner:

|  | A | B | C | D | E | F |
|---|---|---|---|---|---|---|
| Gallopamil.HCl | 100 | 100 | 100 | 100 | 100 | 100 |
| Na alginate | 300 | 240 | 200 | 166 | 132 | 332 |
| ®Eudragit E | 32 | 92 | 132 | 166 | 200 | 0 |
| PVP | 13 | 13 | 13 | 13 | 13 | 13 |
| Mg stearate | 4 | 4 | 4 | 4 | 4 | 4 |
| Cellulose powder | 31 | 31 | 31 | 31 | 31 | 31 |

For this purpose, gallopamil.HCl, Na alginate and ®Eudragit E are dry-blended in a mixer, moistened with an aqueous solution of PVP or PVP/PVA copolymers (®Kollidon 30, ®Kollidon 25 or ®Kollidon VA 64) while stirring, forced through a sieve and dried in a fluidized-bed drier, passed again through a sieve and mixed with Mg stearate and cellulose powder. The mixtures were pressed to give tablets weighing 480 mg.

Barucainide was processed similarly.

The hardness of the tablets was determined using the ®Pharmatest hardness tester and their abrasion was measured with the ®Pharmatest friabilator (400 revolutions in 13 minutes).

The following results were obtained:

| Tablets | A | B | C | D | E | F |
|---|---|---|---|---|---|---|
| Hardness (N) | 104 | 122 | 137 | 103 | 84 | 61 |

-continued

| Tablets | A | B | C | D | E | F |
|---|---|---|---|---|---|---|
| Abrasion (%) | 0.1 | 0.1 | 0.1 | 1.0 | 1.0 | 3.8 |

Similar values were obtained when gallopamil was replaced with another active compound, e.g. barucainide, or another ®Eudragit (e.g. ®Eudragit RS) was used instead of ®Eudragit E.

EXAMPLE 2

If the mixtures A to F of Example 1 are pressed directly without granulation to give tablets, the resulting tablets have a hardness of from 70 to 110N. Mixture F, however, gives unusable tablets having a hardness of only 10N.

EXAMPLE 3

Tablets having the following composition (in mg) were prepared similarly to Example 1:

|  | G | H |
|---|---|---|
| Gallopamil | 100 | 100 |
| Na alginate | 267 | 267 |
| ®Eudragit RS | 67 | — |
| PVP | 13 | 13 |
| Mg stearate | 4 | 4 |
| Cellulose powder | 29 | 29 |

Tablets G had a hardness of 120N and tablets H had a hardness of 78N. The corresponding values for the friability were 0.05% and 2.1%, respectively.

If the tablets are produced by direct compression, i.e. without granulation, tablets having a hardness of 100N (G) or 13N (H) are obtained. Testing the tablets Test persons each received 1 tablet G or H (cf. Example 3). Blood samples were then taken at certain time intervals and the content of gallopamil therein was determined:

| Time (h) | 0.5 | 1 | 2 | 3 | 4 | 6 | 8 | 10 | 12 |
|---|---|---|---|---|---|---|---|---|---|
| G (ng/ml of plasma) | 0.7 | 0.9 | 4.6 | 6.8 | 10 | 9.0 | 8.9 | 8.2 | 5.9 |
| H (ng/ml of plasma) | 3.8 | 10 | 29 | 33 | 36 | 17 | 10 | 6.4 | 6.9 |

In contrast to H, G has a substantially flatter plasma level curve.

EXAMPLE 4

Tablets having the following composition (in mg) were prepared:

|  | J | K |
|---|---|---|
| Propafenone.HCl | 600 | 600 |
| Na alginate | 253 | 253 |
| ®Eudragit RS | 53 | — |
| Cellulose | 11 | 11 |
| PVP | 20 | 20 |
| Mg stearate | 3 | 3 |

The preparation was carried out by moist granulation of a mixture of propafenone and alginate (in case J also with ®Eudragit) with an aqueous PVP solution and subsequent addition of cellulose and Mg stearate to the dried granules. The granules were converted into tablets similarly to Example 1.

In case J, the tablets obtained had a hardness of 165N and their friability was virtually impossible to measure. In case K, the tablets obtained were unusable and did not withstand subsequent film coating without giving a fairly large amount of fragments. The application of a rapidly dissolving film is absolutely essential for masking the extremely bitter flavor of propafenone.

The ®Eudragit E and RS trademark have the following meaning. ®Eudragit RS is a copolymer of acrylic and methacrylic acid esters with a small amount of a quaternary ammonium group of the formula

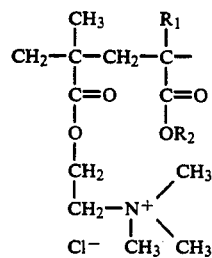

$R_1 = H, CH_3$
$R_2 = CH_3, C_2H_5$ in which the mol ratio of the ammonium group to the remaining neutral (meth)acrylic acid esters is near 1:40. The average molecular weight is about 150,000. ®Eudragit E is a copolymer with cationic character on the basis of dimethylaminoethylmethacrylate and neutral methacrylic acid esters representedly the formula

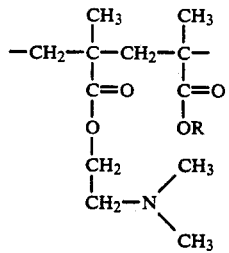

$R = CH_3, C_4H_9$ in which the average molecular weight is near 150,000.

We claim:

1. A tablet for sustained release of a drug selected from the group consisting of gallopamil and propafenone composed of a blend of a unit dosage of the drug with a mixture of alginate and a polyacrylate in a ratio of 15:1 to 2:1 wherein the polyacrylate is a copolymer of neutral (meth)acrylic acid esters of methanol, ethanol and trimethylammonioethanol chloride wherein the ratio of the ammonium group containing ester unit to the remaining neutral (meth)acrylic acid ester units is about 1:40.

* * * * *